United States Patent [19]

Lagerwall

[11] Patent Number: 5,793,449
[45] Date of Patent: Aug. 11, 1998

[54] PROTECTIVE DEVICE

[75] Inventor: Sven T. Lagerwall, Göteborg, Sweden

[73] Assignee: Optrel AG, Wattwil, Sweden

[21] Appl. No.: 545,789

[22] PCT Filed: May 9, 1997

[86] PCT No.: PCT/SE94/00427

§ 371 Date: Dec. 13, 1995

§ 102(e) Date: Dec. 13, 1995

[87] PCT Pub. No.: WO94/27180

PCT Pub. Date: Nov. 24, 1994

[30] Foreign Application Priority Data

May 10, 1993 [SE] Sweden ............... 9301605-3

[51] Int. Cl.$^6$ .......................... G02F 1/1335
[52] U.S. Cl. ............................ 349/14
[58] Field of Search ............... 349/13, 14, 74

[56] References Cited

U.S. PATENT DOCUMENTS

| | | | |
|---|---|---|---|
| 3,873,804 | 3/1975 | Gordon | 349/14 |
| 4,071,912 | 2/1978 | Budmiger | 349/14 |
| 4,155,122 | 5/1979 | Budmiger | 349/14 |
| 4,728,173 | 3/1988 | Toth . | |
| 4,904,065 | 2/1990 | Yuasa et al. . | |

FOREIGN PATENT DOCUMENTS

| | | |
|---|---|---|
| 2735985 | 3/1979 | Germany . |
| 4106019 | 10/1991 | Germany . |
| 4038498 | 6/1992 | Germany . |

OTHER PUBLICATIONS

Patent Abstracts of Japan, Vol. 14, No. 360, P-1088, abstract of JP. A. 2-132417 (Baiotoron K.K.), May 21, 1990.

*Primary Examiner*—William L. Sikes
*Assistant Examiner*—James A. Dudek
*Attorney, Agent, or Firm*—Beveridge, DeGrandi, Weilacher & Young, L.L.P

[57] ABSTRACT

The invention relates to a protective device of the type having a body (1) and a filtering unit (10) supported by said body and acting as a visor, said filtering unit being electrically shiftable between at least two light transmitting conditions and comprising, for this purpose, one or more LC cells. The filtering unit (10) is made wholly or at least to a major extent of polymer material and is designed as a panoramic visor which is darkenable over its entire area. Said one or more LC cells are in the form of a foil and extend over the entire area of the panoramic visor. The invention is of special interest for welding helmets with automatically controlled darkening.

17 Claims, 2 Drawing Sheets

PROTECTIVE DEVICE

The present invention relates to a protective device comprising a body and a filtering unit supported by the body and acting as a visor, said filtering unit being electrically shiftable between at least two light transmitting conditions and comprising, for this purpose, one or more liquid crystal cells, in the following called LC cells.

The invention is specifically developed for welding helmets with automatic darkening and will therefore be described below with reference to this application, but it will be appreciated that also other applications are possible within the scope of the invention, such as helmet visors for pilots, motor cyclists etc.

Protective devices of the type mentioned by way of introduction are described in U.S. Pat. No. 3,873,804 (filed in 1973, inventor M. Gordon) which discloses an eye piece of a welding helmet, comprising a liquid-crystal-based electro-optical cell (EO cell) in combination with a light-controlled electric circuit. In response to welding light, the EO cell is caused to change from a light transmitting condition to a light blocking condition. The EO cell is composed of two parallel glass plates, and the space between these plates is filled with a nematic liquid crystal material with a dielectric anisotropism, called TN type liquid crystal. On the interior surfaces of the glass plates are transparent electrodes to be applied to an electric field across the nematic liquid crystal for shifting the degree of light rotation of the liquid crystal. Outside of the glass plates are polarisers which in combination with the light rotation condition of the nematic liquid crystal permits or counteracts light transmission through the eye piece. As illustrated in FIG. 1 of U.S. Pat. No. 3,873,804, the eye piece is arranged as a rectangular window in the front side of the welding helmet in front of the welder's eyes.

A development of the welding helmet in U.S. Pat. No. 3,873,804 is disclosed in U.S. Pat. No. 4,039,254 (filed in 1976, inventor M. Gordon), using two or more EO cells and at least three polarisers arranged in tandem, thereby achieving a higher degree of darkening in the light blocking condition. Also in this patent, use is made of a nematic liquid crystal material between glass plates. The eye piece shape and position on the welding helmet are essentially the same as in U.S. Pat. No. 3,873,804.

A further prior art darkening device for a welding helmet of essentially the same construction as the device of U.S. Pat. No. 4,039,254 is disclosed in SE 425,048 (filed in 1978, inventor A. G. Hornell). This device comprises, in turn, a first polariser, a first EO cell, a second polariser, a second EO cell, and a third polariser. Like in the above-mentioned U.S. patents, each EO cell consists of two flat, parallel glass plates, the space between the plates enclosing a liquid crystal consisting of a nematic material with a dielectric anisotropism. FIG. 4 of SE 425,048 illustrates how the light-controlled eye piece, like in the above-mentioned patents, is arranged as a rectangular window in the front side of the welding helmet.

EP-A1-0,157,744 (filed in 1985, inventor P. Toth) discloses a darkening device for welding helmets, comprising two EO cells of which at least one is of the nematic type with an admixture of dichroic colouring agents with anisotropic light absorption (so-called guest-host design). A filter disc in the ray path eliminates residual light from the "colour cell" in the light blocking condition thereof. Like in the above-mentioned patents, the EO cells of EP-A1-0,157,744 are composed of parallel glass plates and in the space between the glass plates, nematic liquid crystals. Like in the above-mentioned variants, the eye piece is designed as a rectangular window in the front side of the welding helmet, as shown in FIG. 1 of EP-A1-0,157,744.

The above welding helmets with automatic darkening have successively been developed towards improved contrast and improved rapidity. There remains however a serious drawback of these prior art devices, viz. that they afford the user a most unsatisfactory viewing angle, i.e. merely objects positioned essentially immediately in front of the welder can be viewed through the optical means, which is a consequence of the optical means being designed as a relatively small, flat window in the front side of the welding helmet.

The object of the invention therefore is to provide an improved protective device of the type mentioned by way of introduction, with an improved viewing angle and with retained possibility of electrically shifting the transmission degree of the filtering unit.

According to the present invention, this and other objects are achieved by a protective device of the type mentioned by way of introduction, which is characterised in that the filtering unit is made wholly or at least to a major extent of polymer material and designed as a panoramic visor which is darkenable over its entire area, and that said one or more LC cells are in the form of a foil and extend over the entire area of the panoramic visor.

By LC cell is, according to the present invention, meant an optoelectric unit comprising a liquid crystal, surrounding layers if necessary, transparent electrode layers for applying an electric field across the liquid crystal, and the necessary polarisers. Electrode layers and polarisers may optionally be common to a number of LC cells.

In the present application, the term "panoramic visor" means a form which is essentially concave towards the user, such as a surface curved in one plane or two intersecting planes, alternatively a stepwise flat surface, comprising side portions, thereby permitting the darkenable surface of the filtering unit to cover at least the major part of the user's normal field of vision.

In addition to the protective device according to the invention resulting in a significantly increased viewing angle as compared to the prior art devices, a plurality of other essential advantages are achieved over prior art. Since the filtering unit according to the invention is made wholly or at least to a major extent of polymer material, the total weight of the device will be lower, at the same time as the weight balance of the entire device is improved. The filtering unit can be made entirely of polymer material in case all liquid crystals included are polymeric, but even if normal, i.e. monomeric liquid crystals are included in the filtering unit, the latter will have a total weight which is considerably lower than that of the prior art filtering units with glass plates. A further advantage is that the invention permits reduced power requirement, which will be discussed in more detail below. One more advantage of using LC cells in the form of a foil in the filtering unit is that the active area of the filtering unit can be made considerably larger as compared to today's filtering units based on glass plates. Moreover, a protective device according to the invention will be significantly more shock resistant than prior art devices.

In a preferred embodiment of the invention, the filtering unit comprises two or more LC cells, neighbouring LC cells in the filtering unit optionally having a common polariser.

The combination liquid crystal/polymer is at present to be found in the following three embodiments 1–3. For each of these embodiments 1–3, different types of liquid crystal can be used. In welding, the most important ones are (i)

twisted nematic (=TN), (ii) smectic C* type (=ferroelectric), and (iii) smectic A* type (=paraelectric). These liquid crystal types (i), (ii) and (iii) can further be present in their "pure" form or with an admixture of dichroic colouring agent molecules (guest-host design).

1. "LC Foil" (Liquid Crystal Foil). In this embodiment, a normal liquid crystal, i.e. a monomer liquid crystal, is arranged between two polymer foils which are preferably coated with conductive electrode layers. Spacer elements can be arranged between the polymer foils. The extinction (darkening) is high in this embodiment.

2. "PLC" (Polymer Liquid Crystal). In this embodiment, the actual liquid crystal is in polymeric form, which means that surrounding polymer foils or films are not necessary. However, the term "PLC" in the present application should be considered also to comprise the alternative polymer liquid crystal with surrounding polymer foils or films. In the PLC embodiment, only smectic liquid crystal materials can be used for the invention, such as C* or A*. The change-over time of polymeric nematic material is extremely long, i.e. in the order of 1 sec. or more. Thus, for a welding application use can be made of a so-called FLCP design with a polymeric version of smectic C* type material (ferroelectric). Especially, FLCP has excellent bistability (memory function) which can be used for the present invention since electric operation is required but at the actual change-over moment, which results in reduced power requirement.

3. "PDLC" (Polymer Dispersed Liquid Crystal). This embodiment is not applicable to the invention, since it changes between transparent and dispersing conditions.

For each LC cell included in the filtering unit according to the invention, it is thus possible to select either embodiment No. 1—LC foil—or embodiment No. 2—PLC.

Said one or more LC cells in the filtering unit can comprise at least one LC cell containing a smectic liquid crystal which can be ferroelectric, especially C* type, or paraelectric, especially A* type.

Said one or more LC cells of the filtering unit may comprise at least one LC cell containing a TN type liquid crystal.

In a particularly preferred embodiment of the invention, the filtering unit comprises at least two LC cells, a first LC cell comprising a C* type smectic liquid crystal designed as a uniform polymer foil (embodiment No. 2—FLCP), and a second LC cell comprising a TN type liquid crystal disposed in a space between two spaced-apart polymer foils (embodiment No. 1—LC foil with TN crystal). The TN cell can, on the one hand, function as the "safety cell" of the filtering unit, i.e. operate with parallel polarisers to provide extinction in case of power failure and, on the other hand, serve to produce a continuously adjustable grey scale. However, the TN cell is slower than the FLCP cell. The latter will therefore act as a "fast shutter" in the filtering unit. Moreover, the contrast of the FLCP cell is more independent of direction as compared to the TN cell.

In case the protective device according to the invention is used as a welding helmet, it preferably comprises control means, including light detecting means, adapted to shift, in a per se known manner, in response to light from a welding arc, the filtering unit from a condition with relatively high light transmission, to a condition with relatively low light transmission. Such control means do not per se constitute part of the present invention and are therefore not described in more detail. Control circuits as described in the above-mentioned patents are fundamentally useful, however possibly modified in case bistable LC cells are used and control voltages can possibly be restricted to the actual moments of change-over.

Further features and embodiments of the invention are defined in the appended claims and the following description of an embodiment of the invention, reference being made to the accompanying drawings.

Figure 1:
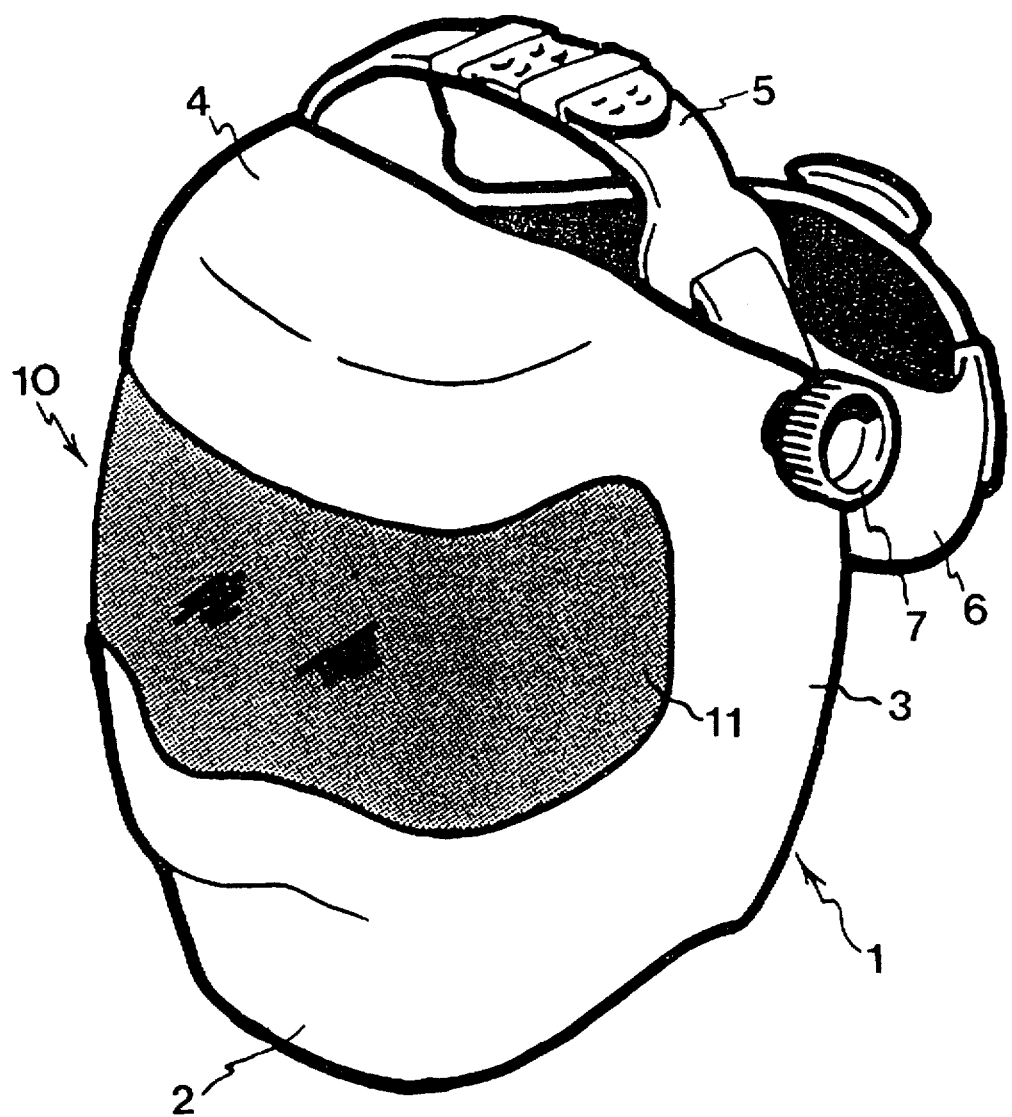
FIG. 1 is a perspective view of a protective device according to the invention designed as a welding helmet.

The welding helmet in FIG. 1 comprises a body generally designated 1, which has the shape of a mask and comprises a front side 2, side portions 3 and a top portion 4. The body 1 is in prior art manner fitted with adjustable fastening straps 5 and 6 which are pivotally connected to the body 1 via two tensioning knobs 7 of which only one is shown. The body 1 can preferably be made of a rigid plastic material of limited weight.

The front side 2 and the side portions 3 of said body are formed with an opening into which a filtering unit generally designated 10 is fitted, which along its circumference is attached to the body 1 in some suitable manner. The filtering unit 10 is electrically shiftable between at least two light transmitting conditions and comprises, for this purpose, one or more LC cells whose design will be described in more detail below.

As is apparent from FIG. 1, the filtering unit 10 is designed as a panoramic visor which covers essentially the welder's entire field of vision and especially comprises side members 11 inserted in the side portions 3 of the body 1. The filtering unit 10 is made wholly or at least to a major part of polymer material, and especially said LC cells are in the form of a foil and extend over the entire area of the panoramic visor.

UV filters and IR filters can be arranged in some suitable manner, preferably integrated with and formed according to the filtering unit 10 designed as a panoramic visor.

A welding helmet according to the construction in FIG. 1 yields an excellent weight balance and a low total weight, at the same time as the darkenable area of the welding helmet, i.e. the surface of the filtering unit 10, extends over essentially the entire field of vision of the welder.

The shape of the body 1 and the visor 10 may of course be varies in many ways within the scope of the invention, and therefore the shape illustrated in FIG. 1 is to be considered but a nonrestrictive embodiment. Especially, the filtering unit 10 can take up a larger or a smaller part of the total surface of the welding helmet as compared to the embodiment in FIG. 1.

Further, the welding helmet in FIG. 1 is provided with control means (not shown) comprising photocells or the like, which are adapted to darken, in response to welding light, the filtering unit 10 to a suitable extent. No detailed description of these control means is required, since the construction and function thereof fall within the scope of knowledge of a man skilled in the art.

Figure 2:
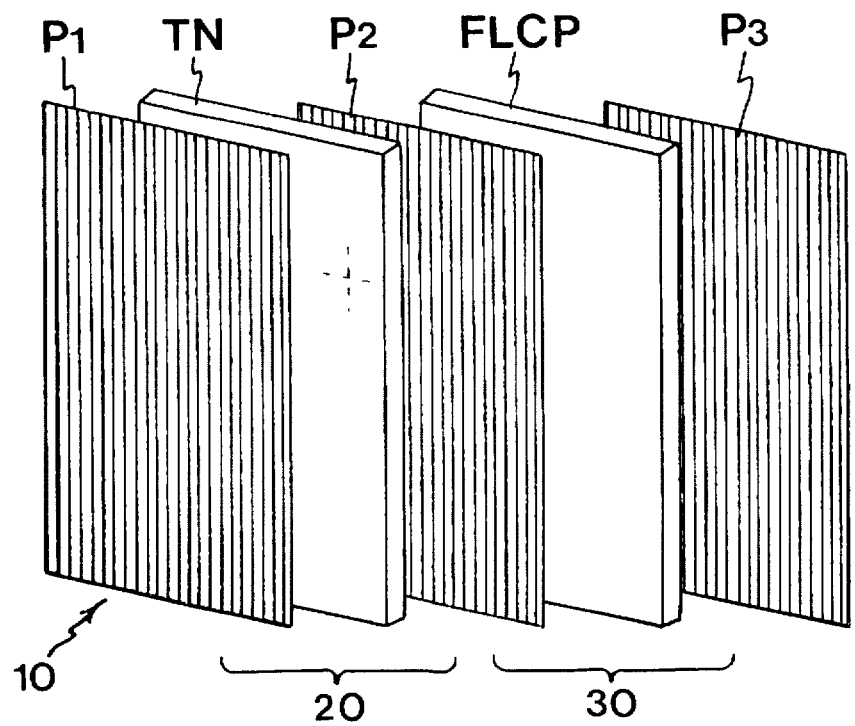
FIG. 2 is a schematic exploded view of an embodiment of a filtering unit which is useful for the welding helmet in FIG. 1.

FIG. 2 is a schematic exploded view of a filtering unit 10 to be used in the welding helmet in FIG. 1. FIG. 2 is schematic in so far as the individual components are shown spaced apart and plane-parallel, whereas in reality these components engage with each other and are curved according to the shape of the panoramic visor.

The filtering unit 10 in FIG. 2 comprises a first LC cell 20 of a design having a TN type liquid crystal disposed in a space between two spaced-apart polymer foils, i.e. the above-mentioned embodiment No. 1. To this TN cell belong two parallel polarisers $P_1$ and $P_2$, the optical axis of the TN cell extending in parallel with or perpendicular to the polarising direction of the polarisers $P_1$ and $P_2$, as indicated by dashed lines in FIG. 2.

The visor 10 in FIG. 2 further comprises a second LC cell 30 of a design having a polymer C* type ferroelectric liquid crystal designed as a uniform polymer foil, i.e. an FLCP cell according to embodiment No. 2 as described above. To this FLCP cell 30 belong two polarisers $P_2$ and $P_3$, the polariser $P_2$ being common to the two cells 20 and 30.

In the embodiment in FIG. 2, the FLCP cell 30 acts as the fast shutter of the filtering unit 10, while the TN cell 20 on the one hand acts as a safety cell (no or just low transmission in the event of power failure) and, on the other hand, permits grey scale adjustment by suitable adjusting means.

Figure 3:
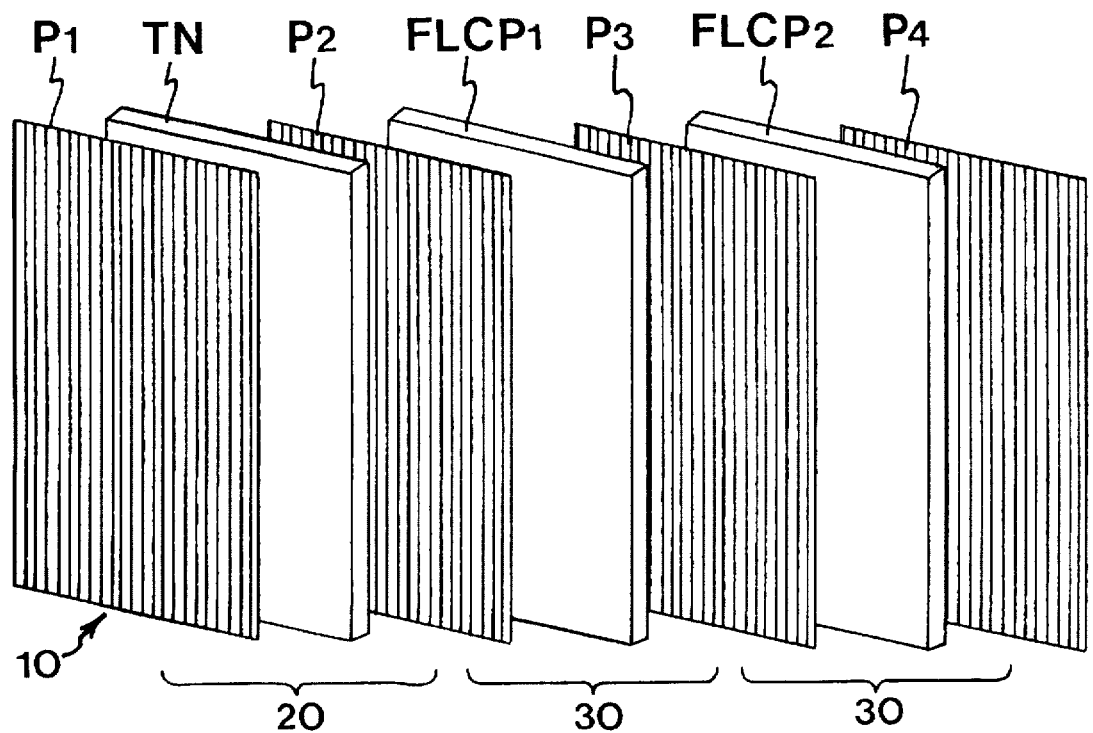
FIG. 3 is a schematic exploded view of an alternative embodiment of the filtering unit in FIG. 2.

FIG. 3 is a schematic exploded view of a variant of the filtering unit 10 in FIG. 1. The filtering unit 10 in FIG. 3 comprises a TN cell 20 according to FIG. 2 and two FLCP cells 30 designated $FLCP_1$ and $FLCP_2$, which allows faster change-over operation, especially if restricted change-over angles (18–25 degrees) are selected for each FLCP cell. For the FLCP cells in FIG. 3 use can be made of C*+C*, but also C*+A* or A*+A*.

It is understood that the sequence of the cells in FIGS. 2 and 3 may be varied, and that the choice of material and the design can be changed within the scope of the appended claims.

I claim:

1. Protective device comprising a body (1) and a filtering unit (10) supported by said body (1) and acting as a visor, said filtering unit being electrically operable between at least two light transmitting conditions and comprising, for this purpose, at least two LC cells, characterised in that said filtering unit (10) is made wholly or at least to a major extent of polymer material and designed as a panoramic visor which is darkenable over its entire area, and said LC cells are in the form of a foil and extend over the entire area of the panoramic visor, and said LC cells comprise a first LC cell (30) containing a C* type smectic liquid crystal designed as a uniform polymer foil (FLCP), and a second LC cell (20) containing a TN type liquid crystal disposed in a space between two spaced-apart polymer foils (LC foil).

2. Protective device as claimed in claim 1, characterised in that said LC cells further comprised at least one LC cell containing a paraelectric smectic liquid crystal.

3. Protective device as claimed in claim 2, characterised in that said paraelectric smectic liquid crystal contains A* type material.

4. Protective device as claimed in claim 1, characterised in that the surface of the panoramic visor is curved in one plane.

5. Protective device as claimed in claim 1, characterised in that the surface of the panoramic visor is curved in two intersecting planes.

6. Protective device as claimed in claim 1 for use as a welding helmet, characterised by control means comprising light detecting means which are adapted to shift, in response to light from a welding arc, said filtering unit from a condition with relatively high light transmission to a condition with relatively low light transmission.

7. Protective device comprising a body (1) and a filtering unit (10) supported by said body (1) and acting as a visor, said filtering unit being electrically operable between at least two light transmitting conditions and comprising, for this purpose, at least two LC cells, characterised in that said filtering unit (10) is made wholly or at least to a major extent of polymer material and designed as a panoramic visor which is darkenable over its entire area, and said LC cells are in the form of a foil and extend over the entire area of the panoramic visor, and said LC cells comprise at least one LC cell (30) containing a paraelectric smectic liquid crystal.

8. Protective device as claimed in claim 7, characterised in that said paraelectrical smectic liquid crystal contains A* type material.

9. Protective device as claimed in claim 7, characterised in that said LC cells comprise at least one LC cell (20) of a design having a liquid crystal disposed in a space between two spaced-apart polymer foils (LC foil).

10. Protective device as claimed in claim 7, characterised in that said LC cells comprise at least one LC cell (30) of a design having a polymer liquid crystal shaped as a uniform polymer foil (PLC).

11. Protective device as claimed in claim 7, characterised in that said LC cells further comprise at least one LC cell containing a ferroelectric smectic liquid crystal.

12. Protective device as claimed in claim 11, characterised in that said ferroelectric liquid crystal contains C* type material.

13. Protective device as claimed in claim 7, characterised in that said LC cells further comprise at least one LC cell containing a TN type liquid crystal.

14. Protective device as claimed in claim 7, characterised in that said LC cells comprise a first LC cell (30) containing a C* type smectic liquid crystal designed as a uniform polymer foil (FLCP), and a second LC cell (20) containing a TN type liquid crystal disposed in a space between two spaced-apart polymer foils (LC foil).

15. Protective device as claimed in claim 7, characterised in that the surface of the panoramic visor is curved in one plane.

16. Protective device as claimed in claim 7, characterised in that the surface of the panoramic visor is curved in two intersecting planes.

17. Protective device as claims in claim 7 for use as a welding helmet, characterised by control means comprising light detecting means which are adapted to shift, in response to light from a welding arc, said filtering unit from a condition with relatively high light transmission to a condition with relatively low light transmission.

* * * * *

UNITED STATES PATENT AND TRADEMARK OFFICE
CERTIFICATE OF CORRECTION

PATENT NO.   : 5,793,449
DATED        : August 11, 1998
INVENTOR(S)  : LAGERWALL It is certified that error appears in the above-indentified patent and that said Letters Patent is hereby corrected as shown below:

On the Cover Page item [22] should be as follows:

[22] PCT filed: May 9, 1994

Signed and Sealed this

Fifteenth Day of June, 1999

Attest:

Q. TODD DICKINSON

*Attesting Officer*   Acting Commissioner of Patents and Trademarks